(12) United States Patent
Tsuchiya et al.

(10) Patent No.: US 7,105,319 B2
(45) Date of Patent: Sep. 12, 2006

(54) OLIGONUCLEOTIDES FOR DETECTING TUBERCLE BACILLUS AND METHOD THEREFOR

(75) Inventors: Shigeo Tsuchiya, Tokyo (JP);
Noriyoshi Masuda, Tokyo (JP);
Takahiro Maruyama, Kanagawa (JP);
Takao Matsuba, Kanagawa (JP);
Takahiko Ishiguro, Kanagawa (JP)

(73) Assignee: Tosoh Corporation, Shinnanyo (JP)

( * ) Notice: Subject to any disclaimer, the term of this patent is extended or adjusted under 35 U.S.C. 154(b) by 525 days.

(21) Appl. No.: 10/381,256

(22) PCT Filed: Jul. 24, 2002

(86) PCT No.: PCT/JP02/07508

§ 371 (c)(1),
(2), (4) Date: Mar. 24, 2003

(87) PCT Pub. No.: WO03/010309

PCT Pub. Date: Feb. 6, 2003

(65) Prior Publication Data

US 2004/0087782 A1 May 6, 2004

(30) Foreign Application Priority Data

Jul. 25, 2001 (JP) ............................. 2001-224436
Aug. 8, 2001 (JP) ............................. 2001-240874

(51) Int. Cl.
*C12P 19/34* (2006.01)

(52) U.S. Cl. ........................ 435/91.2; 435/6; 536/23.1; 536/23.7

(58) Field of Classification Search ..................... None
See application file for complete search history.

(56) References Cited

FOREIGN PATENT DOCUMENTS

| EP | 1 055 734 A2 | * | 11/2000 |
| WO | WO 95/31570 A1 | * | 11/1995 |
| WO | EP 1 002 878 A2 | * | 5/2000 |
| WO | WO 00/75371 A1 | * | 12/2000 |
| WO | WO 03/010309 A1 | * | 2/2003 |

OTHER PUBLICATIONS

Andersen et al, Infect. Immun. 57:2481 (1989).*

G. M. E. Van Der Vliet, et al., Journal of General Microbiology, vol. 139 (Pt 10), pp. 2423-2429, "Nucleic Acid Sequence-Based Amplification (NASBA) for the Identification of *Mycobacteria*", 1993.

Lin I. J., et al., Changgeng Yi Xue Za Zhi, 22(2): 204-11, PMID: 10493024, "Comparison of the Sensitivity and Specificity of an Automatic Ligase Chain Reaction Assay System With a One-Step Polymerase Chain Reaction Assay in the Diagnosis of *Mycobacterium tuberculosis* Complex", Jun. 1999 (submitting PubMed Abstract only, 1 page).

E. A. Sweet-Cordero, et al., Tuber Lung Dis., 77 (6): 496-501, PMID: 9039441, 1 page, "Burden of *Mycobacterium tuberculosis* in Sputum Samples Can Be Reliably Determined Using a Quantitative, Non-Redioactive Polymerase Chain Reaction Assay", Dec. 1996 (submitting PubMed Abstract only, 1 page).

H. Koga, Kekkaku, 70 (10): 601-6, PMID: 8523854, "The Application of Molecular Biology to the Diagnosis of *Mycobacteriosis*", Oct. 1995 (submitting PubMed Abstract only, 1 page).

CD-ROM containing an unbridged electronic version of the article on the "Preparation and Utilization of Isolated and Purified Oligonucleotides" by Dr. Andrew Chin.

Francesca Mariani, et al., "*Mycobacterium tuberculosis* H37Rv comparative gene-expression analysis in synthetic medium and human macrophage", Gene, Elsevier Biomedical Press., vol. 253, No. 2, XP-004215732, Aug. 8, 2000, pp. 281-291.

G. Zambardi, et al., "Comparison of three primer sets for the detection of *Mycobacterium tuberculosis* in clinical samples by polymerase chain reaction", Annales de Biologie Clinique, vol. 51, No. 10-11, XP-009050704, 1993, pp. 893-897.

E.A. Sweet-Cordero, et al., "Burden of *Mycobacterium tuberculosis* in sputum samples can be reliably determined using a quantitative, non-radioactive polymerase chain reaction assay", Tubercle and Lung Disease, Churchill Livingstone Medical Journals, vol. 77, No. 6, XP-004540712, Dec. 1996, pp. 496-501.

* cited by examiner

*Primary Examiner*—James Martinell
(74) *Attorney, Agent, or Firm*—Oblon, Spivak, McClelland, Maier & Neustadt, P.C.

(57) ABSTRACT

An oligonucleotide, capable of specific cleavage and amplification of a pab gene which codes for pab, an antigenic protein of *Mycobacterium tuberculosis*, or an RNA derived therefrom, as well as being useful in high sensitive detection and identification thereof, is provided. Further, a combination of oligonucleotides, useful in specific amplification, high sensitive detection and identification of an RNA derived from *Mycobacterium tuberculosis* pab gene as well as a process for detecting *Mycobacterium tuberculosis* by using said combination, are provided.

4 Claims, 3 Drawing Sheets

OLIGONUCLEOTIDES FOR DETECTING TUBERCLE BACILLUS AND METHOD THEREFOR

FIELD OF THE INVENTION

The present invention relates to oligonucleotides and a method for detecting *Mycobacterium tuberculosis* in clinical examination. The oligonucleotides provided in the present invention are useful as reagents for genetic diagnosis which involves procedures such as cleavage, amplification and detection of RNA or DNA, and as reagents for inhibiting reverse transcription or translation of RNA. In particular, the sequences of the oligonucleotides provided in the present invention are useful for reagents or the like for quantitative determination and detection of *Mycobacterium tuberculosis*.

PRIOR ART

Notwithstanding the significant reduction of the occurrence of tuberculosis, it is becoming a serious subject of discussion since its morbidity in the older people has recently increased and, also, it may result in a mass infection among young people who have not experienced tuberculous infection before. The usual examination methods for *Mycobacterium tuberculosis* were based on smear test or culture test. However, since the growth of *Mycobacterium tuberculosis* is slow, it takes more than 4 weeks to obtain results.

Recently, genetic detection kits for detecting tubercle bacillus are commercially available. Included therein is a kit which performs a DNA amplification, in which the detection is carried out by amplifying a genomic DNA coding for 16S rRNA with PCR, followed by hybridization with a specific DNA probe, and a kit which performs the detection by EIA, in which a gene coding for the protein antigen b (hereafter, referred to as "pab"), an antigenic protein of *Mycobacterium tuberculosis*, having a known sequence (Inf. and Immun. 57, 2481–2488, 1989), is amplified with a ligase chain reaction (LCR method). For details, see U.S. Pat. No. 5,631,130. Although these detection methods are automated or semi-automated, as their detection time requires in the order of 4 to 6 hours, they are not suitable in a case where urgent treatment is required. Further, since a DNA amplification process cannot distinguish living bacteria from dead bacteria, it is not suitable in a case, for example, where observation of the effect of an antibiotic is being carried out.

Reverse Transcription-Polymerase Chain Reaction (RT-PCR) is known as a process for amplifying a specific sequence of an RNA. This method amplifies the specific DNA sequence by a process comprising of synthesizing a cDNA from the target RNA in a reverse transcription step, and then amplifying the specific sequence of said cDNA by repetition of a cycle comprising heat denaturation, primer annealing and extension reactions, in the presence of a pair of primers complementary and homologous to both ends of the specific sequence of said cDNA (the antisense primer may be the same as the one used in the reverse transcription step) as well as a thermostable DNA polymerase. However, RT-PCR method requires a two-step operation (a reverse transcription step and a PCR step) as well as an operation involving repetition of rapidly increasing and decreasing the temperature, which prevents its automation.

Therefore, the examination methods used so far do not meet the needs in the clinical practice where speedy detection of tubercle bacillus or speedy confirmation of the treatment is required. Accordingly, a more rapid and highly sensitive detection which would detect only living bacteria is desired. In addition, in order to simplify the examination, an examining instrument which carries out the detection automatically is desired.

It is possible to provide a highly sensitive detection method by use of a process of amplifying the target nucleic acid. As processes for amplifying a specified RNA sequence, NASBA and 3SR methods are known, whereby the specific RNA sequence is amplified by the concerted action of a reverse transcriptase and an RNA polymerase. In these methods, the following steps are carried out: using the target RNA as a template, a double-stranded DNA including a promoter sequence is synthesized with a primer containing the promoter sequence, reverse transcriptase and Ribonuclease H; this double-stranded DNA is used as a template in synthesizing an RNA containing a specific sequence of the target RNA with an RNA polymerase and, subsequently, this RNA provides a template in a chain reaction for synthesizing a double-stranded DNA containing the promoter sequence.

NASBA, 3SR, and the like, allow amplification at a constant temperature and are considered suitable for automation.

Because these amplification methods involve relatively low temperature reactions (41° C., for example), however, the target RNA may form an intramolecular structure that inhibits binding of the primer, which may reduce the reaction efficiency. Therefore, they require subjecting the target RNA to heat denaturation prior to the amplification reaction so as to destroy the intramolecular structure thereof and thus improve the primer binding efficiency. Furthermore, an oligonucleotide capable of binding to an RNA that has formed the intramolecular structure mentioned above is also desired when carrying out the detection of the RNA at a low temperature.

Thus, the first object of the present invention is to provide an oligonucleotide capable of cleaving and amplifying a pab gene which codes for an antigenic protein of *Mycobacterium tuberculosis*, pab, or an RNA derived from said gene, as well as being useful in highly sensitive detection and identification of said gene or RNA. Also, the present invention provides an oligonucleotide useful as a reagent for inhibiting reverse transcription or translation of an RNA. Further, the second object of the present invention is to provide preferable combination of oligonucleotides capable of specifically amplifying an RNA derived from said pab gene at a relatively low temperature (41° C., for example) as well as useful in carrying out a highly sensitive detection and identification of said RNA.

DISCLOSURE OF INVENTION

The first embodiment of the present invention, which has been accomplished to achieve the first object mentioned above, relates to an oligonucleotide for cleavage, detection or amplification of pab gene, a gene element of *Mycobacterium tuberculosis*, which codes for an antigenic protein, pab, or an RNA derived from said gene, which oligonucleotide is capable of binding specifically to said pab gene or RNA derived therefrom, and comprises at least 10 contiguous bases of any of the sequences listed as SEQ. ID. Nos. 1 to 20, or an oligonucleotide complementary to said oligonucleotide.

The second embodiment of the present invention, which has been accomplished to achieve the first object mentioned above, relates to the oligonucleotide according to said first embodiment, wherein said oligonucleotide is an oligonucleotide primer for DNA elongation reaction.

The third embodiment of the present invention, which has been accomplished to achieve the first object mentioned above, relates to the oligonucleotide according to said first embodiment, wherein said oligonucleotide is an oligonucleotide probe of which a portion is modified or labeled with a detectable marker.

The fourth embodiment of the present invention, which has been accomplished to achieve the first object mentioned above, relates to the oligonucleotide according to said first embodiment, wherein said oligonucleotide is a synthetic oligonucleotide in which a portion of its base(s) is(are) modified without impairing the function of said oligonucleotide as an oligonucleotide probe.

The first embodiment of the present invention, which has been accomplished to achieve the second object mentioned above, relates to an RNA amplification process, comprising the steps of: forming a cDNA with an RNA-dependent DNA polymerase using a specific sequence of an RNA derived from Mycobacterium tuberculosis pab gene as a template, with a first primer having a sequence homologous to said specific sequence and a second primer having a sequence complementary to said specific sequence, wherein either the first or second primer has a sequence having the RNA polymerase promoter sequence added at its 5'-region, thereby producing an RNA-DNA double-strand; digesting the RNA of said RNA-DNA double-strand with Ribonuclease H to form a single-stranded DNA; and then forming a double-stranded DNA that includes the promoter sequence allowing transcription of said specific sequence or an RNA comprising a sequence complementary to said specific sequence with a DNA-dependent DNA polymerase using said single-stranded DNA as a template, said double-stranded DNA produces an RNA transcription product in the presence of an RNA polymerase, and said RNA transcription product is subsequently used as the template for the cDNA synthesis with said RNA-dependent DNA polymerase; said process is characterized in that an oligonucleotide comprising at least 10 contiguous bases of any of the sequences listed as SEQ. IDs. No.28 to No.33 is used as the first primer and an oligonucleotide comprising at least 10 contiguous bases of any of the sequences listed as SEQ. IDs. No.34 to No.41 having a sequence complementary to a portion of the RNA sequence of the Mycobacterium tuberculosis pab gene to be amplified is used as the second primer, wherein either the first or second primer includes the RNA polymerase promoter sequence at its 5'-region.

The second embodiment of the present invention, which has been accomplished to achieve the second object mentioned above, relates to the method according to said first embodiment, wherein said amplification process is carried out in the presence of an oligonucleotide capable of specifically binding to the RNA transcription product resulting from said amplification and labeled with an intercalator fluorescent pigment, and changes in the fluorescent properties of the reaction solution is measured, with the proviso that the labeled oligonucleotide has a sequence different from those of the first or second primer.

The third embodiment of the present invention, which has been accomplished to achieve the second object mentioned above, relates to the method according to said second embodiment, characterized in that said oligonucleotide is designed so as to complementarily bind to a least a portion of the sequence of said RNA transcription product, and the fluorescent property changes relative to that of a situation where a complex formation is absent.

The fourth embodiment of the present invention, which has been accomplished to achieve the second object mentioned above, relates to the method according to said third embodiment, characterized in that said oligonucleotide comprises at least 10 contiguous bases of any of the sequences listed as SEQ. IDs. No.42 to No.44 or its complementary sequence.

BEST MODE FOR CARRYING OUT THE INVENTION

As mentioned above, the first object of the present invention is to provide an oligonucleotide capable of cleaving and amplifying a pab gene which codes for an antigenic protein of Mycobacterium tuberculosis, pab, or an RNA derived from said gene, as well as being useful in highly sensitive detection and identification of said gene or RNA.

The oligonucleotides of the invention are oligonucleotides that complementary bind in a specific manner to intramolecular structure-free regions of the target RNA in the aforementioned RNA amplification, and they are capable of binding specifically to the target RNA without heat denaturation described above. In this manner, the present invention provides oligonucleotides that binds to intramolecular structure-free regions of the Mycobacterium tuberculosis RNA at a relatively low and constant temperature (35–50° C., and preferably 41° C.), which are useful for specific cleavage, amplification, detection or the like of Mycobacterium tuberculosis RNA. More specifically, the present invention relates to oligonucleotide probes for cleaving said target RNA at specific site, oligonucleotide primers for amplifying said target DNA with PCR, oligonucleotide primers for amplifying said target RNA with NASBA or the like, and oligonucleotides which accomplish rapidly and highly sensitive detection by using them as oligonucleotide probes for detecting the target nucleic acid without or after performing these amplifications.

SEQ. IDs. No.1 through No.20 illustrate the oligonucleotides of the present invention useful in cleavage, amplification, detection or the like of RNA derived from *Mycobacterium tuberculosis*. In this connection, RNA derived from *Mycobacterium tuberculosis* also includes RNA that has been produced by using this gene as a template. Although each of the oligonucleotide of the present invention may include entire base sequence of any of SEQ IDs No. 1 to No. 20, since an order of 10 bases is adequate for specific binding to an RNA derived from *Mycobacterium tuberculosis*, these oligonucleotides can be ones comprising at least 10 contiguous bases of the described sequences.

The oligonucleotides of the present invention can be used, for example, as probes for cleaving RNA. In the case of cleaving the target RNA at a specific site, this can be accomplished merely by hybridizing the oligonucleotides of the present invention to single-stranded target RNA, and then treating it with an enzyme which digests only the RNA portion of the double-stranded RNA-DNA. As this enzyme, typically, an enzyme known to have Ribonuclease H activity may be used.

Each oligonucleotide of the present invention can be used, for example, as an oligonucleotide primer for nucleic acid amplification. If a nucleic acid amplification method is carried out using the oligonucleotide of the present invention as the primer, it would be possible to amplify only the target nucleic acid, namely *Mycobacterium tuberculosis* nucleic acid. Although examples of amplification methods include PCR, LCR, NASBA and 3SR, nucleic acid amplification methods that can be carried out at a constant temperature such as LCR, NASBA and 3SR are particularly preferable. *Mycobacterium tuberculosis* can be detected by detecting the amplification product by various methods. In this case, any of the above oligonucleotides other than the oligonucleotide used in the amplification may be used as the probe, and the fragment of the amplified specific sequence can be confirmed by electrophoresis or the like.

Each oligonucleotide of the present invention can be used as a probe by, for example, modifying its portion or labeling it with a detectable marker. When detecting the target nucleic acid, the oligonucleotide of the present invention labeled with the detectable marker may be hybridized to a single-stranded target nucleic acid, after which the hybridized probe can be detected via the marker. The marker detection may be carried out by a method suitable for the particular marker, and for example, when using an intercalator fluorescent dye for labeling the oligonucleotide, a dye with the property of exhibiting increased fluorescent intensity by intercalation in the double-stranded nucleic acid comprising the target nucleic acid and the oligonucleotide probe may be used in order to allow easy detection of only the hybridized probe without removal of the probe that has not hybridized to the target nucleic acid. When using a common fluorescent dye as the marker, the marker may be detected after removal of the probe that has not hybridized to the target nucleic acid. For the detection, the target nucleic acid in the sample is preferably amplified to a detectable amount by a nucleic acid amplification method such as PCR, NASBA or 3SR method, among which isothermal nucleic acid amplification methods such as the NASBA and 3SR methods are most preferable. Alternatively, when incorporating the oligonucleotide-labeled probe in the reaction solution during the amplification, it is especially preferable to modify the probe by, for example, adding glycolic acid to the 3'-end so that the probe will not function as a nucleotide primer.

As mentioned above, the second object of the present invention is to provide preferable combinations of oligonucleotides capable of specifically amplifying an RNA derived from said pab gene at a relatively low temperature (41° C., for example) as well as useful in carrying out a highly sensitive detection and identification of said RNA.

The invention related to this second object provides a nucleic acid amplification process for amplifying an RNA derived from *Mycobacterium tuberculosis* pab gene, and a method for detecting an RNA transcription product produced by this nucleic acid amplification process. This nucleic acid amplification process includes PCR, NASBA or 3SR method, among which isothermal nucleic acid amplification methods such as the NASBA and 3SR methods, which amplifies the RNA derived from *Mycobacterium tuberculosis* pab gene by use of a concerted action of a reverse transcriptase and an RNA polymerase (by reacting the reverse transcriptase and the RNA polymerase under a condition to provide a concerted action), are mostly preferable.

For example, in the amplification process of the NASBA method, an RNA derived from *Mycobacterium tuberculosis* pab gene present in a sample is used as a template for synthesis of a DNA employing an RNA-dependent DNA polymerase, the RNA of the double-stranded RNA/DNA is digested by Ribonuclease H to produce a single-stranded DNA, the single-stranded DNA is then used as a template for production of a double-stranded DNA having a promoter sequence capable of transcribing RNA comprising the specific sequence or a sequence complementary to said specific sequence employing a DNA-dependent DNA polymerase, the double-stranded DNA produces an RNA transcription product in the presence of an RNA polymerase, and the RNA transcription product is then used as a template for cDNA synthesis employing the RNA-dependent DNA polymerase. The present invention is characterized in that an oligonucleotide comprising at least 10 contiguous bases of any of the sequences listed as SEQ. IDs. No.28 to No.33 having a sequence homologous to a portion of the RNA sequence of the *Mycobacterium tuberculosis* pab gene to be amplified is used as the first primer and an oligonucleotide comprising at least 10 contiguous bases of any of the sequences listed as SEQ. IDs. No.34 to No.41 having a sequence complementary to a portion of the RNA sequence of the *Mycobacterium tuberculosis* pab gene is used as the second primer, wherein either the first or second primer has the RNA polymerase promoter sequence at its 5'-region.

Although there are no particular restrictions on the RNA-dependent DNA polymerase, the DNA-dependent DNA polymerase and the ribonuclease H to be used in the present invention, it is preferable to use AMV reverse transcriptase having all of these types of activity. Moreover, although the RNA polymerase to be used in the present invention is not particularly restricted, T7 phage RNA polymerase or SP6 phage RNA polymerase is preferably used.

In the amplification process of the present invention, an oligonucleotide that is complementary to the region adjacent to and overlapping with the 5' end region of the specific sequence (bases 1 to 10) of the RNA derived from *Mycobacterium tuberculosis* pab gene is added, and the RNA derived from *Mycobacterium tuberculosis* pab gene is cleaved with Ribonuclease H at the 5' end region of the specific sequence to give the initial template for nucleic acid amplification, thereby allowing amplification even for an RNA derived from *Mycobacterium tuberculosis* pab gene without having the specific sequence positioned at its 5' end. The oligonucleotide used for the cleaving may, for example, be any of those listed as SEQ. IDs No. 22 to No. 27, provided that it differs from the one used as the second primer in the amplification process. In addition, the oligonucleotide for cleaving is preferably chemically modified (for example, aminated) at the 3' hydroxyl group in order to prevent an extension reaction from the 3' end.

Although the amplification product obtained by the above amplification process can be detected by any known method, per se, it is preferable to carry out the detection, in the presence of an oligonucleotide probe labeled with an intercalator fluorescent pigment, by measuring changes in the fluorescent properties of the reaction solution. This oligonucleotide may be one in which the intercalator fluorescent pigment is bonded to a phosphorous atom in the oligonucleotide through a linker. The oligonucleotide is characterized in that when it forms a double-stranded chain with the target nucleic acid, separation analysis is not required because the intercalator portion intercalates into the double-stranded chain portion to vary the fluorescent characteristics (Ishiguro, T. et al. (1996), Nucleic Acids Res. 24 (24) 4992–4997).

The oligonucleotide sequence is not critical so long as it has a sequence complementary to at least a portion of the amplification product. However, the oligonucleotide sequence is preferably one comprising at least 10 contiguous bases of the sequence listed as SEQ. IDs. No. 42 to No. 44, or complementary sequence thereof. Moreover, chemical modification (for example, glycolic acid addition) at the 3' end hydroxyl group of the oligonucleotide is preferred in order to inhibit an extension reaction based on the oligonucleotide used as a primer.

Accordingly, it becomes possible to amplify and detect an RNA having the same sequence as the specific sequence of an RNA derived from *Mycobacterium tuberculosis* pab gene in a single tube at a constant temperature and in a single step, and, thus, the amplification process is easily automated.

The present invention will now be explained in greater detail by way of examples, with the understanding that the invention is not limited by the examples.

EXAMPLES

Example 1

Oligonucleotides which specifically bind to *Mycobacterium tuberculosis* pab-RNA at 41° C. were selected. The pab-RNA is a synthesized and purified RNA obtained by in vitro transcription using double-stranded DNA containing the pab-RNA base sequence as the template.

(1) A sample of a standard RNA (SEQ. ID No.21) comprising bases No. 111 to No. 1436 of pab-RNA derived from *Mycobacterium tuberculosis* pab gene (the RNA base sequence numbering is in accordance with Inf. and Immun. 57, 2481–2488 (1989)) was quantified by ultraviolet absorption at 260 nm, and then diluted with an RNA diluent (10 mM Tris-HCl buffer (pH 8.0), 0.1 mM EDTA, 1 mM DTT, 0.5 U/µl RNase Inhibitor (Takara Shuzo Co., Ltd.) to 1.53 pmol/µl.

(2) Next, a reaction solution in an amount of 14 µl having the following composition was dispensed into 0.5 ml volume PCR tubes (GeneAmp Thin-Walled Reaction™ Tubes; Perkin-Elmer Co., Ltd.).

Reaction Solution Composition (Each concentration designating one in a final reaction solution in an amount of 15 µl)

| 60 mM | Tris-HCl buffer (pH 8.6) |
| 17 mM | magnesium chloride |
| 90 mM | potassium chloride |
| 39 U | RNase inhibitor (Takara Shuzo Co., Ltd.) |

-continued

| 1 mM | DTT |
| 0.066 µM | standard RNA |
| | distilled water for adjusting volume |
| 0.2 µM | oligonucleotide solution (one of the oligonucleotides shown below was used) |

MP-1R (oligonucleotide complementary to bases No.216 to No.236 of *Mycobacterium tuberculosis* pab gene; SEQ. ID. No. 1)

MP-2R (oligonucleotide complementary to bases No.268 to No.288 of *Mycobacterium tuberculosis* pab gene; SEQ. ID. No. 2)

MP-3R (oligonucleotide complementary to bases No.319 to No.339 of *Mycobacterium tuberculosis* pab gene; SEQ. ID. No. 3)

MP-4R (oligonucleotide complementary to bases No.455 to No.476 of *Mycobacterium tuberculosis* pab gene; SEQ. ID. No. 4)

MP-5R (oligonucleotide complementary to bases No.484 to No.504 of *Mycobacterium tuberculosis* pab gene; SEQ. ID. No. 5)

MP-6R (oligonucleotide complementary to bases No.498 to No.517 of *Mycobacterium tuberculosis* pab gene; SEQ. ID. No. 6)

MP-7R (oligonucleotide complementary to bases No.535 to No.554 of *Mycobacterium tuberculosis* pab gene; SEQ. ID. No. 7)

MP-8R (oligonucleotide complementary to bases No.675 to No.697 of *Mycobacterium tuberculosis* pab gene; SEQ. ID. No. 8)

MP-9R (oligonucleotide complementary to bases No.712 to No.731 of *Mycobacterium tuberculosis* pab gene; SEQ. ID. No. 9)

MP-10R (oligonucleotide complementary to bases No.724 to No.743 of *Mycobacterium tuberculosis* pab gene; SEQ. ID. No. 10)

MP-11R (oligonucleotide complementary to bases No.757 to No.778 of *Mycobacterium tuberculosis* pab gene; SEQ. ID. No. 11)

MP-12R (oligonucleotide complementary to bases No.790 to No.809 of *Mycobacterium tuberculosis* pab gene; SEQ. ID. No. 12)

MP-13R (oligonucleotide complementary to bases No.937 to No.956 of *Mycobacterium tuberculosis* pab gene; SEQ. ID. No. 13)

MP-14R (oligonucleotide complementary to bases No.961 to No.982 of *Mycobacterium tuberculosis* pab gene; SEQ. ID. No. 14)

MP-15R (oligonucleotide complementary to bases No.1011 to No.1030 of *Mycobacterium tuberculosis* pab gene; SEQ. ID. No. 15)

MP-16R (oligonucleotide complementary to bases No.1071 to No.1093 of *Mycobacterium tuberculosis* pab gene; SEQ. ID. No. 16)

MP-17R (oligonucleotide complementary to bases No.1103 to No.1123 of *Mycobacterium tuberculosis* pab gene; SEQ. ID. No. 17)

MP-18R (oligonucleotide complementary to bases No.1166 to No.1185 of *Mycobacterium tuberculosis* pab gene; SEQ. ID. No. 18)

MP-19R (oligonucleotide complementary to bases No.1256 to No.1278 of *Mycobacterium tuberculosis* pab gene; SEQ. ID. No. 19)

MP-20R (oligonucleotide complementary to bases No.1270 to No.1290 of *Mycobacterium tuberculosis* pab gene; SEQ. ID. No. 20)

(3) The reaction solutions were then incubated at 41° C. for 5 minutes, and then 1 μl of 8 U/μl AMV-Reverse transcriptase (Takara Shuzo Co., Ltd.; an enzyme that cleaves the RNA of DNA/RNA double strands) was added.

(4) Subsequently, the PCR tubes were incubated at 41° C. for 10 minutes.

(5) Urea-polyacrylamide gel (acrylamide concentration: 6%, urea: 7 M) electrophoresis was conducted to confirm the cleaved fragments after the reaction. Dyeing following the electrophoresis was carried out with SYBR Green II™ (Takara Shuzo Co., Ltd.). Upon binding of the oligonucleotide to the specific site of the target RNA, the RNA of the DNA/RNA double strands is cleaved by the ribonuclease H activity of AMV transcriptase. As a result, a characteristic band could be observed.

Figure 1:
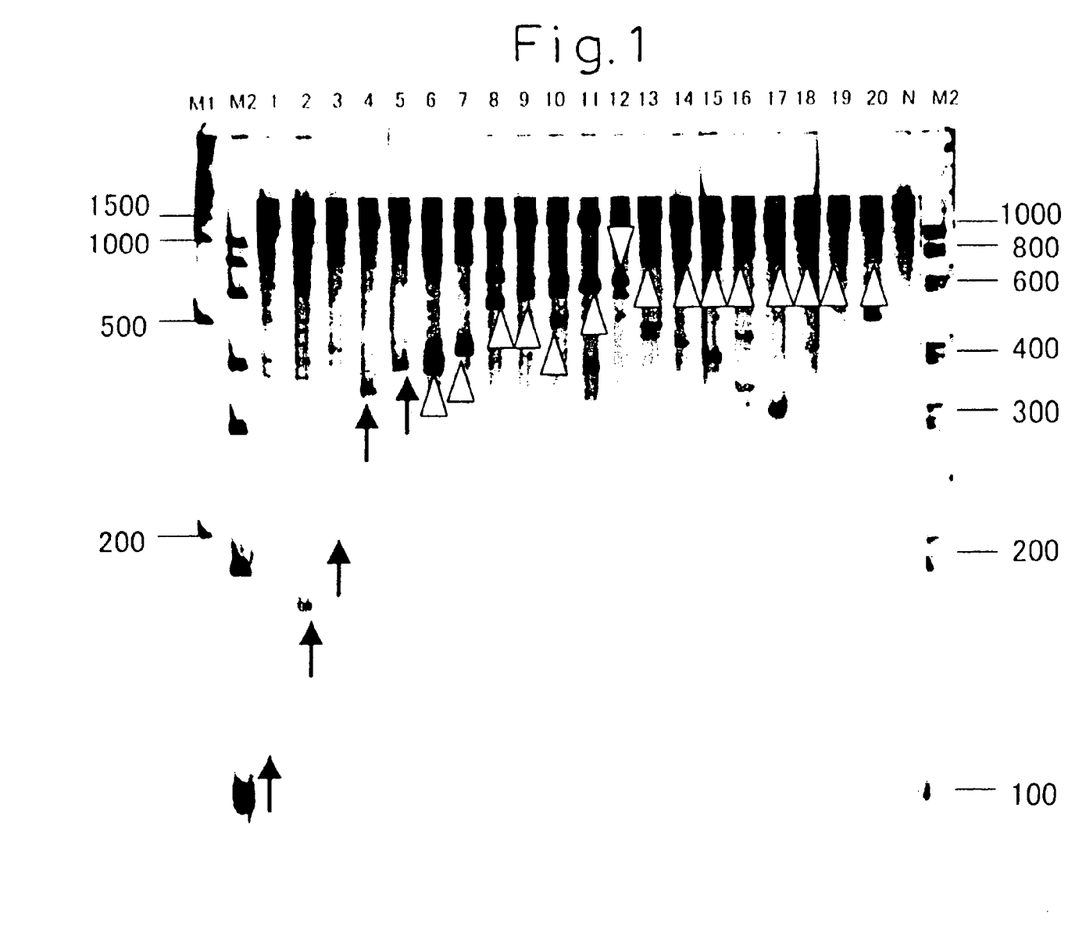
FIG. 1 is a urea modified 6% polyacrylamide electrophoresis diagram for samples obtained by performing binding tests on a standard RNA of Mycobacterium tuberculosis pab gene at 41° C., using oligonucleotides MP-1R to MP-20R (black and white are inverted). The arrows show the positions of the specific bands. Lanes 1 to 20 show the results of the binding tests using MP-1R to MP-20R, respectively, and lane N is a result for a negative control test (using the diluent instead of RNA samples). RNA markers (0.1 to 1 kb, and 0.2 to 10 kb) were used as the molecular markers (Lanes M1 and M2).

The results of electrophoresis are shown in FIG. 1 (black and white inverted). When the oligonucleotide specifically binds to the standard RNA, the standard RNA will be digested in this binding region, yielding digestion products having characteristic chain lengths. Table 1 shows the positions and expected band chain lengths resulting when the oligonucleotide specifically binds to the standard RNA. Specific bands were confirmed for MP-1R, MP-2R, MP-4R, MP-6R, MP-7R, MP-8R, MP-9R, MP-12R, MP-13R, MP-14R, MP-15R, MP-17R and MP-18R. It was demonstrated that the oligonucleotides strongly bind to the *Mycobacterium tuberculosis* pab gene RNA at 41° C. in a constant state. The base numbers shown in Table 1 represent those in the base sequence of the *Mycobacterium tuberculosis* pab gene. Further, the circles in the Table represent that only specific bands had been observed, and the crosses therein represent that both specific and nonspecific bands had been observed.

TABLE 1

| Oligonucleotide | Base positions | Expected cleaved band lengths (base) | Result |
| --- | --- | --- | --- |
| MP-1R | 206–236 | 111, 1200 | ○ |
| MP-2R | 268–288 | 163, 1148 | ○ |
| MP-3R | 319–339 | 214, 1097 | X |
| MP-4R | 454–476 | 350, 960 | ○ |
| MP-5R | 484–504 | 379, 932 | X |
| MP-6R | 498–517 | 393, 919 | ○ |
| MP-7R | 535–554 | 430, 882 | ○ |
| MP-8R | 674–697 | 570, 739 | ○ |
| MP-9R | 712–730 | 607, 705 | ○ |
| MP-10R | 724–743 | 619, 693 | X |
| MP-11R | 757–778 | 652, 658 | X |
| MP-12R | 790–809 | 685, 627 | ○ |
| MP-13R | 937–956 | 832, 343 | ○ |
| MP-14R | 961–982 | 856, 454 | ○ |
| MP-15R | 1011–1030 | 906, 406 | ○ |
| MP-16R | 1071–1093 | 966, 343 | X |
| MP-17R | 1103–1123 | 998, 313 | ○ |
| MP-18R | 1166–1185 | 1061, 251 | ○ |
| MP-19R | 1256–1278 | 1151, 158 | X |
| MP-20R | 1270–1290 | 1165, 146 | X |

As explained above, the oligonucleotides of the present invention are oligonucleotides that complementary bind to RNA derived from pab gene, which is a genetic element of *Mycobacterium tuberculosis*, even under conditions of relatively low and constant temperature (35–50° C., preferably 41° C.), which tend to cause an intramolecular structure in RNA and prevent binding of primers and probes thereto. Specific binding of the oligonucleotides is therefore possible without heat denaturation of the target RNA. The oligonucleotides of the invention are thus useful as oligonucleotides for cleavage, amplification, detection or the like of RNA derived from *Mycobacterium tuberculosis* pab gene, i.e. as oligonucleotide primers or oligonucleotide probes to be used in RNA amplification methods.

Furthermore, the oligonucleotides of the invention are also clearly useful for amplification and detection of *Mycobacterium tuberculosis* pab gene. Oligonucleotides complementary to the above-mentioned oligonucleotides are also useful for amplification of double-stranded DNA by the PCR method, or for detection of cDNA obtained by reverse transcription of RNA.

The oligonucleotides of the invention are not limited to the specifically listed base sequences (between 20 and 23 mers), and they may be oligonucleotides comprising at least 10 or more contiguous bases within those sequences. This is obvious from the fact that 10 mer base sequences are sufficient to ensure adequate specificity of primers or probes to target nucleic acids under relatively low temperature condition (preferably, at 41° C.).

Example 2

An RNA amplification reaction was carried out using oligonucleotide probes which specifically bind to an RNA derived from *Mycobacterium tuberculosis* pab gene.

(1) A standard RNA (1326 mer) (SEQ. ID No.21) comprising bases No. 111 to No. 1436 of pab-RNA derived from *Mycobacterium tuberculosis* pab gene was diluted to a concentration of $10^3$ copies/5 μl with an RNA diluent (10 mM Tris-HCl buffer (pH 8.0), 1 mM EDTA, 0.5 U/μl RNase Inhibitor (Takara Shuzo Co., Ltd.; 5 mM DTT). In the control testing sections, only the diluent was used (negative).

(2) A reaction solution in an amount of 20 μl having the following composition was dispensed into 0.5 ml volume PCR tubes (Gene Amp Thin-Walled Reaction Tubes, Perkin-Elmer Co., Ltd.). Then, the above RNA sample in an amount of 5 μl was added.

Reaction Solution Composition (Each concentration designating one in a final reaction solution in an amount of 30 μl)

| | |
| --- | --- |
| 60 mM | Tris-HCl buffer (pH 8.6) |
| 17 mM | magnesium chloride |
| 90 mM | potassium chloride |
| 39 U | RNase Inhibitor |
| 1 mM | DTT |
| 0.25 mM | each of dATP, dCTP, dGTP and dTTP |
| 3.6 mM | ITP |
| 3.0 mM | each of ATP, CTP, GTP and UTP |
| 0.16 μM | of the first oligonucleotide |
| 1.0 μM | of the second oligonucleotide |
| 1.0 μM | of the third oligonucleotide |
| 13% | DMSO |

Distilled water for adjusting volume (3) An RNA amplification reaction was carried out using the oligonucleotides having sequences listed in Table 2 as the first, second and third oligonucleotides. A solution was prepared so that the combination of the first, second and third oligonucleotides became one as listed in Table 2.

(4) After incubating the above reaction solution for 5 minutes at 41° C., 5 μl of an enzyme solution having the following composition was added.

Enzyme Solution Composition (Each concentration designating one in a final reaction solution in an amount of 30 μl)

1.7% sorbitol
3 μg bovine serum albumin
142 U T7 RNA polymerase (Gibco)
8 U AMV-Reverse transcriptase (Takara Shuzo Co., Ltd.)
Distilled water for adjusting volume (5) Subsequently, the PCR tubes were incubated for 30 minutes at 41° C.

(6) In order to identify the RNA amplified portion following the reaction, agarose gel (4% agarose gel) electrophoresis was performed. Dyeing following the electrophoresis was performed with SYBR Green II™ (Takara Shuzo Co., Ltd). When an oligonucleotide binds to the specific portion of the target RNA, the RNA portion sandwiched by the second and third oligonucleotide is amplified, thereby enabling observation of a characteristic band.

Figure 2:
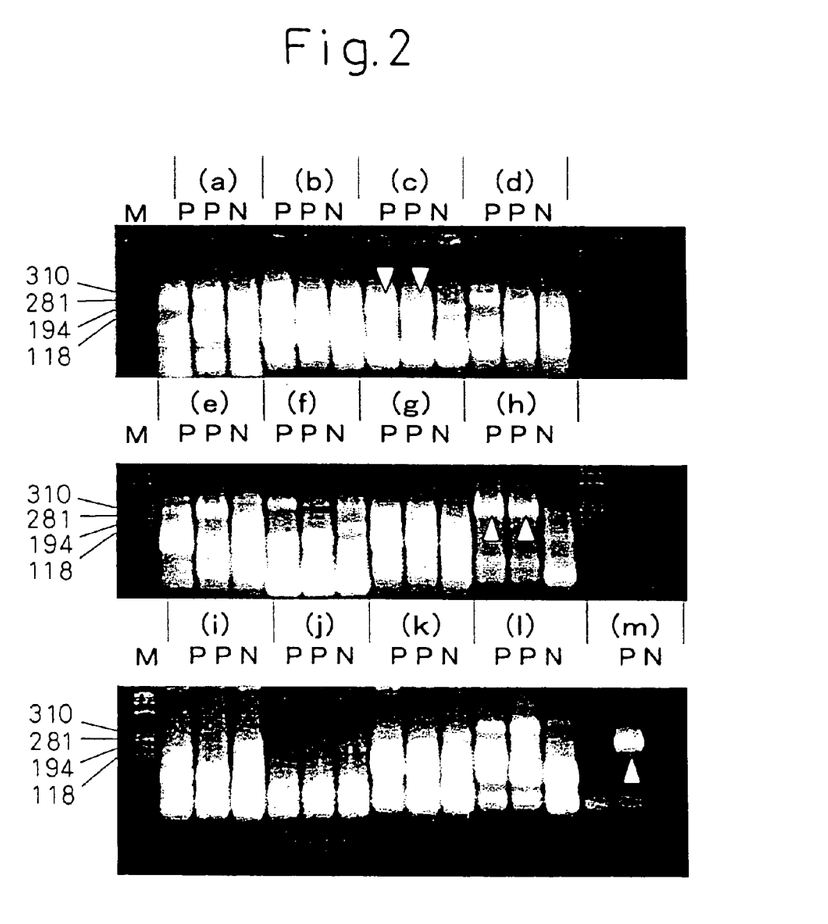
FIG. 2 is an electrophoresis diagram obtained from the RNA amplification reactions in Example 2, employing oligonucleotides combinations (a) to (m) shown in Table 2. In this figure, P represents the result obtained by employing an RNA sample having an initial RNA amount of $10^3$ copies/test, while N is a result for a negative control test (using the diluent instead of RNA samples). ΦX174/Hae III digest (Marker 4) was used as the molecular marker (Lane M).

The results of the electrophoresis are shown in FIG. 2. The chain lengths of the specific bands amplified in the reaction are shown in Table 2. Of the RNA amplification reactions using the combinations of oligonucleotides shown in Table 2, a specific band could be confirmed in combinations (c), (h) and (m). Accordingly, it was demonstrated that these combinations are effective in detecting the *Mycobacterium tuberculosis*.

TABLE 2

| Combination | 1st oligonucleotide | 2nd oligonucleotide | 3rd oligonucleotide | Amplification product chain length (base) |
|---|---|---|---|---|
| (a) | MP-4S | MP-4F | MP-9R | 270 |
| (b) | MP-4S | MP-4F | MP-12R | 348 |
| (c) | MP-13S | MP-13F | MP-17R | 182 |
| (d) | MP-1S | MP-1F | MP-3R | 118 |
| (e) | MP-4S | MP-4F | MP-10R | 282 |
| (f) | MP-4S | MP-4F | MP-11R | 317 |
| (g) | MP-6S | MP-6F | MP-10R | 241 |
| (h) | MP-6S | MP-6F | MP-11R | 276 |
| (i) | MP-9S | MP-9F | MP-16R | 377 |
| (j) | MP-12S | MP-12F | MP-16R | 299 |
| (k) | MP-13S | MP-13F | MP-16R | 152 |
| (l) | MP-13S | MP-13F | MP-20R | 349 |
| (m) | MP-6S | MP-6F | MP-9R | 229 |

Table 2 shows the combinations of the first, second and third oligonucleotides used in the present example, as well as the chain lengths of the amplified specific band resulting from the RNA amplification reactions using these combinations.

The 3' end hydroxyl group of each first oligonucleotide base sequence was aminated. Each second oligonucleotide base sequence includes T7 promoter region in its region of from the 1st "A" to the 28th "A" from the 5' end. The base numbers represent those in the base sequence of the *Mycobacterium tuberculosis* pab gene.

First Oligonucleotide
MP-1S (SEQ. ID. No.22; Bases No. 213 to No. 236)
MP-4S (SEQ. ID. No.23; Bases No. 453 to No. 476)
MP-6S (SEQ. ID. No.24; Bases No. 494 to No. 517)
MP-9S (SEQ. ID. No.25; Bases No. 708 to No. 731)
MP-12S (SEQ. ID. No.26; Bases No. 786 to No. 809)
MP-13S (SEQ. ID. No.27; Bases No. 933 to No. 956)

Second Oligonucleotide
MP-1F (SEQ. ID. No.28; Bases No. 228 to No. 250)
MP-4F (SEQ. ID. No.29; Bases No. 468 to No. 490)
MP-6F (SEQ. ID. No.30; Bases No. 509 to No. 531)
MP-9F (SEQ. ID. No.31; Bases No. 723 to No. 745)
MP-12F (SEQ. ID. No.32; Bases No. 800 to No. 823)
MP-13F (SEQ. ID. No.33; Bases No. 948 to No. 970)

Third Oligonucleotide
MP-3R (SEQ. ID. No.34; Bases No. 319 to No. 339)
MP-9R (SEQ. ID. No.35; Bases No. 712 to No. 731)
MP-10R (SEQ. ID. No.36; Bases No. 724 to No. 743)
MP-11R (SEQ. ID. No.37; Bases No. 757 to No. 778)
MP-12R (SEQ. ID. No.38; Bases No. 790 to No. 809)
MP-16R (SEQ. ID. No.39; Bases No. 1071 to No. 1093)
MP-17R (SEQ. ID. No.40; Bases No. 1103 to No. 1123)
MP-20R (SEQ. ID. No.41; Bases No. 1270 to No. 1290)

Example 3

Detection, in various number of copies of RNA derived from *Mycobacterium tuberculosis* pab gene, was carried out using combinations of oligonucleotides according to the present invention.

(1) A standard RNA of pab-RNA derived from *Mycobacterium tuberculosis* pab gene, as described in Example 2, was diluted to concentrations ranging from $10^1$ copies/5 μl to $10^5$ copies/5 μl with an RNA diluent (10 mM Tris-HCl (pH 8.0), 1 mM EDTA, 0.5 U/μl RNase Inhibitor (Takara Shuzo Co., Ltd.: 5 mM DTT). In the control testing sections, only the diluent was used (negative).

(2) A reaction solution in an amount of 20 μl having the following composition was dispensed into PCR tubes (0.5 ml volume; Gene Amp Thin-Walled Reaction Tubes, Perkin-Elmer Co., Ltd.). Then, the above RNA sample in an amount of 5 μl was added.

Reaction Solution Composition (Each concentration designating one in a final reaction solution in an amount of 30 μl)

| 60 mM | Tris-HCl buffer (pH 8.6) |
|---|---|
| 17 mM | magnesium chloride |
| 150 mM | potassium chloride |
| 39 U | RNase Inhibitor |
| 1 mM | DTT |
| 0.25 mM | each of dATP, dCTP, dGTP and dTTP |
| 3.6 mM | ITP |
| 3.0 mM | each of ATP, CTP, GTP and UTP |

0.16 μM of the first oligonucleotide (MP-13S; SEQ. ID. No.27; wherein its 3' end hydroxyl group is aminated)
1.0 μM of the second oligonucleotide (MP-13F; SEQ. ID. No.33)
1.0 μM of the third oligonucleotide (MP-17R; SEQ. ID. No.40)
25 nM intercalator fluorescent pigment-labeled oligonucleotide (YO-Pab1076-S-G; SEQ. ID. No.42; labeled with an intercalator fluorescent pigment at the phosphorous atom between the 10th "A" and the 11th "T" from the 5' end, and modified with a glycol group at its 3' end hydroxyl group.)
13% DMSO
Distilled water for adjusting volume (3) After incubating the above reaction solution for 5 minutes at 41° C., 5 μl of an enzyme solution having the following composition and pre-incubated for 2 minutes at 41° C. was added.

Enzyme Solution Composition (Each concentration designating one in a final reaction solution in an amount of 30 μl)

1.7% sorbitol
3 μg bovine serum albumin
142 U T7 RNA polymerase (Gibco)
8 U AMV-Reverse transcriptase (Takara Shuzo Co., Ltd.)
Distilled water for adjusting volume (4) The PCR tubes were then incubated at 41° C. using a direct measurable fluorescence spectrophotometer equipped with a temperature controller, and the reaction solution was periodically measured at an excitation wavelength of 470 nm and a fluorescent wavelength of 510 nm.

Figure 3:
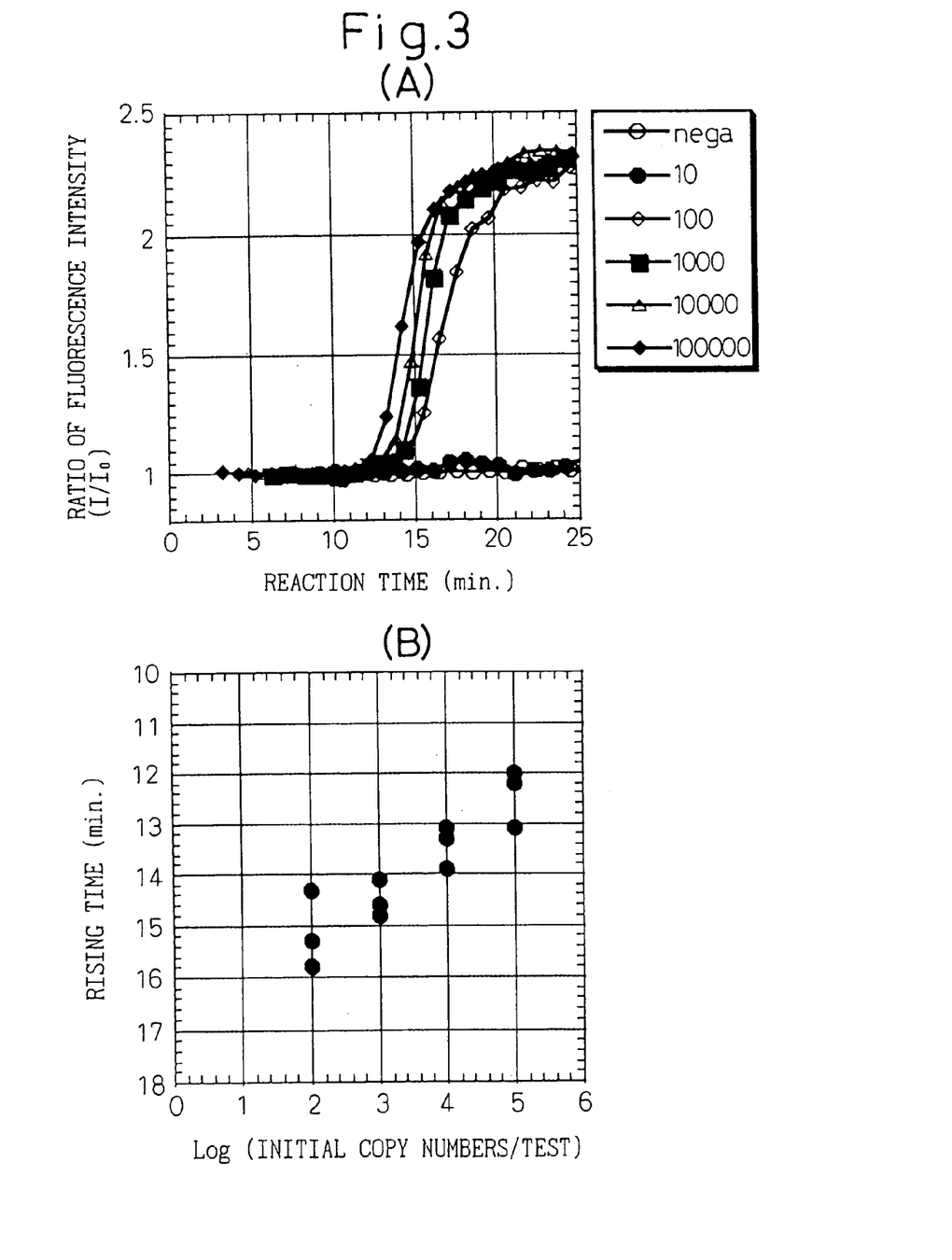
FIG. 3 shows the results obtained in Example 3 employing initial RNA amounts ranging of from $10^1$ copies/test to $10^5$ copies/test. Panel (A) is a fluorescence profile exhibiting the fluorescence increase ratio that increases with the reaction time-course formation of RNA. Panel (B) is a calibration curve resulting from the relationship between the logarithm of initial RNA amount and the rising time. It was demonstrated that RNA with the initial copies of $10^2$ copies/test can be detected by a reaction for about 15 minutes, and that there is a correlation between the initial RNA amount and the rising time.

FIG. 3(A) shows the time-course changes in the fluorescence increase ratio (fluorescence intensity at predetermined time/background fluorescence intensity) of the sample, where enzyme was added at 0 minutes. FIG. 3(B) shows the relationship between the logarithm of the initial RNA amount and the rising time (time at which the relative fluorescence reaches the negative sample's average value plus 3 standard deviations; i.e., the time to reach 1.2). The initial RNA amount was between $10^1$ copies/test and $10^5$ copies/test.

FIG. 3(A) shows that $10^2$ copies were detected in about 15 minutes. A fluorescent profile and a calibration curve both depending on the initial concentration of the labeled RNA was obtained, indicating that it is possible to quantify the target RNA present in unknown samples. This demonstrates that this method allows rapid, highly sensitive detection of *Mycobacterium tuberculosis*.

As has been explained above, the present invention provides useful combinations of oligonucleotide primers or oligonucleotide probes which specifically bind to RNA derived from *Mycobacterium tuberculosis* pab gene, and rapidly amplify and detect the target RNA even under relatively low and constant temperature (35–50° C. and preferably 41° C.) conditions in which RNA in a sample would form an intramolecular structure which inhibit the primer and probe binding.

The base lengths of the oligonucleotides in the combinations of the present invention are not limited to the concretely described lengths, but rather include oligonucleotides comprised of at least 10 contiguous bases within these sequences. This is clear from the fact that a base sequence of about 10 mer is adequate for ensuring specificity of primer or probe to a target nucleic acid under relatively low temperature (preferably 41° C.) conditions.

The invention claimed is:

1. A method for amplifying pab gene, a gene element of *Mycobacterium tuberculosis*, which employs an RNA amplification process, comprising the steps of: forming a cDNA with an RNA-dependent DNA polymerase using a specific sequence of an RNA derived from said pab gene present in a sample as a template, with a first primer having a sequence homologous to said specific sequence and a second primer having a sequence complementary to said specific sequence, wherein either the first or second primer has a sequence having the RNA polymerase promoter sequence added at its 5'-region, thereby producing an RNA-DNA double-strand; digesting the RNA of said RNA-DNA double-strand with Ribonuclease H to form a single-stranded DNA; and then forming a double-stranded DNA that includes the promoter sequence allowing transcription of said specific sequence or an RNA comprising a sequence complementary to said specific sequence with a DNA-dependent DNA polymerase using said single-stranded DNA as a template, said double-stranded DNA produces an RNA transcription product in the presence of an RNA polymerase, and said RNA transcription product is subsequently used as the template for the cDNA synthesis with said RNA-dependent DNA polymerase; said method is characterized in that an oligonucleotide comprising at least 10 contiguous bases of SEQ ID NO: 33 having a sequence homologous to a portion of the RNA sequence of the *Mycobacterium tuberculosis* pab gene to be amplified is used as the first primer and an oligonucleotide comprising at least 10 contiguous bases of SEQ ID NO: 40 having a sequence complementary to a portion of the RNA sequence of the *Mycobacterium tuberculosis* pab gene is used as the second primer.

2. The method according to claim 1, wherein said RNA amplification process is carried out in the presence of an oligonucleotide probe capable of specifically binding to the RNA transcription product resulting from said amplification and labeled with an intercalator fluorescent pigment, and changes in the fluorescent properties of the reaction solution are measured, with the proviso that the labeled oligonucleotide has a sequence different from those of said first and second primers.

3. The method according to claim 2, characterized in that said probe is designed so as to complementary bind to at least a portion of the sequence of said RNA transcription product, and the fluorescent property changes relative to that of a situation where a complex formation is absent.

4. The method according to claim 3, characterized in that said probe has a sequence comprising at least 10 contiguous bases of SEQ ID NO: 42. or a sequence complementary thereto.

* * * * *

SEQUENCE LISTING

```
<160> NUMBER OF SEQ ID NOS: 44

<210> SEQ ID NO 1
<211> LENGTH: 21
<212> TYPE: DNA
<213> ORGANISM: Artificial Sequence
<220> FEATURE:
<223> OTHER INFORMATION: Synthetic DNA

<400> SEQUENCE: 1
gtggtttcga gccacagccc g                                              21

<210> SEQ ID NO 2
<211> LENGTH: 21
<212> TYPE: DNA
<213> ORGANISM: Artificial Sequence
<220> FEATURE:
<223> OTHER INFORMATION: Synthetic DNA

<400> SEQUENCE: 2
ggggtagtcg cgacagtacc g                                              21

<210> SEQ ID NO 3
<211> LENGTH: 21
<212> TYPE: DNA
<213> ORGANISM: Artificial Sequence
<220> FEATURE:
<223> OTHER INFORMATION: Synthetic DNA

<400> SEQUENCE: 3
gggtagagca gcgtgctacc g                                              21

<210> SEQ ID NO 4
<211> LENGTH: 22
<212> TYPE: DNA
<213> ORGANISM: Artificial Sequence
<220> FEATURE:
<223> OTHER INFORMATION: Synthetic DNA
```

```
<400> SEQUENCE: 4
gataggcgtc ggaggcccca at                                              22

<210> SEQ ID NO 5
<211> LENGTH: 21
<212> TYPE: DNA
<213> ORGANISM: Artificial Sequence
<220> FEATURE:
<223> OTHER INFORMATION: Synthetic DNA

<400> SEQUENCE: 5
ttgtgcgcgg ccatatcacc t                                               21

<210> SEQ ID NO 6
<211> LENGTH: 20
<212> TYPE: DNA
<213> ORGANISM: Artificial Sequence
<220> FEATURE:
<223> OTHER INFORMATION: Synthetic DNA

<400> SEQUENCE: 6
gttcatcagc cccttgtgcg                                                 20

<210> SEQ ID NO 7
<211> LENGTH: 20
<212> TYPE: DNA
<213> ORGANISM: Artificial Sequence
<220> FEATURE:
<223> OTHER INFORMATION: Synthetic DNA

<400> SEQUENCE: 7
tgtagttgac ctgctgagcg                                                 20

<210> SEQ ID NO 8
<211> LENGTH: 23
<212> TYPE: DNA
<213> ORGANISM: Artificial Sequence
<220> FEATURE:
<223> OTHER INFORMATION: Synthetic DNA

<400> SEQUENCE: 8
cggaactacc gcggtgccgg gca                                             23

<210> SEQ ID NO 9
<211> LENGTH: 20
<212> TYPE: DNA
<213> ORGANISM: Artificial Sequence
<220> FEATURE:
<223> OTHER INFORMATION: Synthetic DNA

<400> SEQUENCE: 9
agaaggtgtc accggacccg                                                 20

<210> SEQ ID NO 10
<211> LENGTH: 20
<212> TYPE: DNA
<213> ORGANISM: Artificial Sequence
<220> FEATURE:
<223> OTHER INFORMATION: Synthetic DNA

<400> SEQUENCE: 10
actgggtgaa caagaaggtg                                                 20

<210> SEQ ID NO 11
```

```
<211> LENGTH: 22
<212> TYPE: DNA
<213> ORGANISM: Artificial Sequence
<220> FEATURE:
<223> OTHER INFORMATION: Synthetic DNA

<400> SEQUENCE: 11
cttgccccag ccctcgggat ct                                              22

<210> SEQ ID NO 12
<211> LENGTH: 20
<212> TYPE: DNA
<213> ORGANISM: Artificial Sequence
<220> FEATURE:
<223> OTHER INFORMATION: Synthetic DNA

<400> SEQUENCE: 12
ggaagtcgac ggtggtgccg                                                 20

<210> SEQ ID NO 13
<211> LENGTH: 20
<212> TYPE: DNA
<213> ORGANISM: Artificial Sequence
<220> FEATURE:
<223> OTHER INFORMATION: Synthetic DNA

<400> SEQUENCE: 13
tattgcctag ttgggcctcg                                                 20

<210> SEQ ID NO 14
<211> LENGTH: 22
<212> TYPE: DNA
<213> ORGANISM: Artificial Sequence
<220> FEATURE:
<223> OTHER INFORMATION: Synthetic DNA

<400> SEQUENCE: 14
gtcgggcaac aagaaattgc ca                                              22

<210> SEQ ID NO 15
<211> LENGTH: 20
<212> TYPE: DNA
<213> ORGANISM: Artificial Sequence
<220> FEATURE:
<223> OTHER INFORMATION: Synthetic DNA

<400> SEQUENCE: 15
cggggttttc gatgcgaagc                                                 20

<210> SEQ ID NO 16
<211> LENGTH: 23
<212> TYPE: DNA
<213> ORGANISM: Artificial Sequence
<220> FEATURE:
<223> OTHER INFORMATION: Synthetic DNA

<400> SEQUENCE: 16
gtagttgatg atcgggtagc cgt                                             23

<210> SEQ ID NO 17
<211> LENGTH: 21
<212> TYPE: DNA
<213> ORGANISM: Artificial Sequence
<220> FEATURE:
<223> OTHER INFORMATION: Synthetic DNA

<400> SEQUENCE: 17
```
cttttgccgg ttgttgacga t                                              21

<210> SEQ ID NO 18
<211> LENGTH: 20
<212> TYPE: DNA
<213> ORGANISM: Artificial Sequence
<220> FEATURE:
<223> OTHER INFORMATION: Synthetic DNA

<400> SEQUENCE: 18
ttgttgccgt cggtgatcgc                                                20

<210> SEQ ID NO 19
<211> LENGTH: 23
<212> TYPE: DNA
<213> ORGANISM: Artificial Sequence
<220> FEATURE:
<223> OTHER INFORMATION: Synthetic DNA

<400> SEQUENCE: 19
ggctagctgg aaatcgtcgc gat                                            23

<210> SEQ ID NO 20
<211> LENGTH: 21
<212> TYPE: DNA
<213> ORGANISM: Artificial Sequence
<220> FEATURE:
<223> OTHER INFORMATION: Synthetic DNA

<400> SEQUENCE: 20
ggtggtcaac gaggctagct g                                              21

<210> SEQ ID NO 21
<211> LENGTH: 1326
<212> TYPE: RNA
<213> ORGANISM: Mycobacterium tuberculosis

<400> SEQUENCE: 21
gacgccaagc gcggaaauug aagagcacag aaagguaugg

```
acggcuaccc gaucaucaac uacgaguacg ccaucgucaa caaccggcaa aaggacgccg    1020
ccaccgcgca gaccuugcag gcauuucugc acugggcgau caccgacggc aacaaggccu    1080
cguuccucga ccagguucau uuccagccgc ugccgcccgc ggugguaag uugucugacg     1140 cguugaucgc gacgauuucc agcuagccuc guugaccacc acgcgacagc aaccuccguc    1200
gggccaucgg gcugcuuugc ggagcaugcu ggcccgugcc ggugaagucg gccgcgcugg    1260
cccggccauc cggugguugg gugggauagg ugcggugauc ccgcugcuug cgcuggucuu    1320
ggugcu                                                              1326

<210> SEQ ID NO 22
<211> LENGTH: 24
<212> TYPE: DNA
<213> ORGANISM: Artificial Sequence
<220> FEATURE:
<223> OTHER INFORMATION: Synthetic DNA

<400> SEQUENCE: 22
gtggtttcga gccacagccc gccg                                            24

<210> SEQ ID NO 23
<211> LENGTH: 24
<212> TYPE: DNA
<213> ORGANISM: Artificial Sequence
<220> FEATURE:
<223> OTHER INFORMATION: Synthetic DNA

<400> SEQUENCE: 23
gataggcgtc ggaggcccca atgt                                            24

<210> SEQ ID NO 24
<211> LENGTH: 24
<212> TYPE: DNA
<213> ORGANISM: Artificial Sequence
<220> FEATURE:
<223> OTHER INFORMATION: Synthetic DNA

<400> SEQUENCE: 24
gttcatcagc cccttgtgcg cggc                                            24

<210> SEQ ID NO 25
<211> LENGTH: 24
<212> TYPE: DNA
<213> ORGANISM: Artificial Sequence
<220> FEATURE:
<223> OTHER INFORMATION: Synthetic DNA

<400> SEQUENCE: 25
agaaggtgtc accggacccg tcgg                                            24

<210> SEQ ID NO 26
<211> LENGTH: 24
<212> TYPE: DNA
<213> ORGANISM: Artificial Sequence
<220> FEATURE:
<223> OTHER INFORMATION: Synthetic DNA

<400> SEQUENCE: 26
ggaagtcgac ggtggtgccg aagc                                            24

<210> SEQ ID NO 27
<211> LENGTH: 24
<212> TYPE: DNA
<213> ORGANISM: Artificial Sequence
```

```
<220> FEATURE:
<223> OTHER INFORMATION: Synthetic DNA

<400> SEQUENCE: 27
tattgcctag ttgggcctcg ccga                                          24

<210> SEQ ID NO 28
<211> LENGTH: 51
<212> TYPE: DNA
<213> ORGANISM: Artificial Sequence
<220> FEATURE:
<223> OTHER INFORMATION: Synthetic DNA

<400> SEQUENCE: 28
aattctaata cgactcacta tagggagacg aaaccaccga gcggttcgcc t            51

<210> SEQ ID NO 29
<211> LENGTH: 51
<212> TYPE: DNA
<213> ORGANISM: Artificial Sequence
<220> FEATURE:
<223> OTHER INFORMATION: Synthetic DNA

<400> SEQUENCE: 29
aattctaata cgactcacta tagggagaac gcctatctgt cggaaggtga t            51

<210> SEQ ID NO 30
<211> LENGTH: 51
<212> TYPE: DNA
<213> ORGANISM: Artificial Sequence
<220> FEATURE:
<223> OTHER INFORMATION: Synthetic DNA

<400> SEQUENCE: 30
aattctaata cgactcacta tagggagact gatgaacatc gcgctagcca t            51

<210> SEQ ID NO 31
<211> LENGTH: 51
<212> TYPE: DNA
<213> ORGANISM: Artificial Sequence
<220> FEATURE:
<223> OTHER INFORMATION: Synthetic DNA

<400> SEQUENCE: 31
aattctaata cgactcacta tagggagaac accttcttgt tcacccagta c            51

<210> SEQ ID NO 32
<211> LENGTH: 51
<212> TYPE: DNA
<213> ORGANISM: Artificial Sequence
<220> FEATURE:
<223> OTHER INFORMATION: Synthetic DNA

<400> SEQUENCE: 32
aattctaata cgactcacta tagggagatc gacttcccgg cggtgccggg t            51

<210> SEQ ID NO 33
<211> LENGTH: 51
<212> TYPE: DNA
<213> ORGANISM: Artificial Sequence
<220> FEATURE:
<223> OTHER INFORMATION: Synthetic DNA

<400> SEQUENCE: 33
aattctaata cgactcacta tagggagata ggcaatagct ctggcaattt c            51
```

```
<210> SEQ ID NO 34
<211> LENGTH: 21
<212> TYPE: DNA
<213> ORGANISM: Artificial Sequence
<220> FEATURE:
<223> OTHER INFORMATION: Synthetic DNA

<400> SEQUENCE: 34
gggtagagca gcgtgctacc g                                        21

<210> SEQ ID NO 35
<211> LENGTH: 20
<212> TYPE: DNA
<213> ORGANISM: Artificial Sequence
<220> FEATURE:
<223> OTHER INFORMATION: Synthetic DNA

<400> SEQUENCE: 35
agaaggtgtc accggacccg                                          20

<210> SEQ ID NO 36
<211> LENGTH: 20
<212> TYPE: DNA
<213> ORGANISM: Artificial Sequence
<220> FEATURE:
<223> OTHER INFORMATION: Synthetic DNA

<400> SEQUENCE: 36
actgggtgaa caagaaggtg                                          20

<210> SEQ ID NO 37
<211> LENGTH: 22
<212> TYPE: DNA
<213> ORGANISM: Artificial Sequence
<220> FEATURE:
<223> OTHER INFORMATION: Synthetic DNA

<400> SEQUENCE: 37
cttgccccag ccctcgggat ct                                       22

<210> SEQ ID NO 38
<211> LENGTH: 20
<212> TYPE: DNA
<213> ORGANISM: Artificial Sequence
<220> FEATURE:
<223> OTHER INFORMATION: Synthetic DNA

<400> SEQUENCE: 38
ggaagtcgac ggtggtgccg                                          20

<210> SEQ ID NO 39
<211> LENGTH: 23
<212> TYPE: DNA
<213> ORGANISM: Artificial Sequence
<220> FEATURE:
<223> OTHER INFORMATION: Synthetic DNA

<400> SEQUENCE: 39
gtagttgatg atcgggtagc cgt                                      23

<210> SEQ ID NO 40
<211> LENGTH: 21
<212> TYPE: DNA
<213> ORGANISM: Artificial Sequence
<220> FEATURE:
<223> OTHER INFORMATION: Synthetic DNA
```

```
<400> SEQUENCE: 40
cttttgccgg ttgttgacga t                                        21

<210> SEQ ID NO 41
<211> LENGTH: 21
<212> TYPE: DNA
<213> ORGANISM: Artificial Sequence
<220> FEATURE:
<223> OTHER INFORMATION: Synthetic DNA

<400> SEQUENCE: 41
ggtggtcaac gaggctagct g                                        21

<210> SEQ ID NO 42
<211> LENGTH: 20
<212> TYPE: DNA
<213> ORGANISM: Artificial Sequence
<220> FEATURE:
<223> OTHER INFORMATION: Synthetic DNA

<400> SEQUENCE: 42
tcgtagttga tgatcgggta                                          20

<210> SEQ ID NO 43
<211> LENGTH: 20
<212> TYPE: DNA
<213> ORGANISM: Artificial Sequence
<220> FEATURE:
<223> OTHER INFORMATION: Synthetic DNA

<400> SEQUENCE: 43
gttgtagttg acctgctgag                                          20

<210> SEQ ID NO 44
<211> LENGTH: 20
<212> TYPE: DNA
<213> ORGANISM: Artificial Sequence
<220> FEATURE:
<223> OTHER INFORMATION: Synthetic DNA

<400> SEQUENCE: 44
ctgaatgctt tgcgcgtcgg                                          20
```